United States Patent

Rovati et al.

[11] 4,000,297
[45] Dec. 28, 1976

[54] N-P-CHLOROBENZOYL TRYPTOPHANE, SALTS AND COMPOSITIONS THEREOF

[75] Inventors: Luigi Rovati, S. Fruttuoso di Monza (Milan); Giampaolo Picciola, Milan; Francesco Makovec, Taccona (Milan), all of Italy

[73] Assignee: Rotta Research Laboratorium S.p.A., S. Fruttuoso di Monza (Milan), Italy

[22] Filed: Jan. 12, 1976

[21] Appl. No.: 648,359

Related U.S. Application Data

[63] Continuation-in-part of Ser. No. 397,051, Sept. 13, 1973, abandoned, which is a continuation-in-part of Ser. No. 222,668, Feb. 1, 1972, abandoned.

[30] Foreign Application Priority Data

May 18, 1971 Italy .................. 68652/71

[52] U.S. Cl. .................. 424/274; 260/326.14 T
[51] Int. Cl.$^2$ .................. C07D 209/20; A61K 31/40
[58] Field of Search .......... 260/326.14 T; 424/274

[56] References Cited

UNITED STATES PATENTS 2,380,479  7/1945  Stiller .................. 260/326.14 T

FOREIGN PATENTS OR APPLICATIONS 2,138,046  12/1972  France .................. 260/326.14 T

OTHER PUBLICATIONS

Sholat et al., "Chem. Abstracts," vol. 76, p. 15, No. 135,571b and Chem. Subst. Index p. 3645cs (1972).

Gish et al., "Chem. Abstracts," vol. 48, p. 1959d (1954).
Pal et al., "Chem. Abstracts," vol. 52, p. 11171f (1958).
Wright et al., "Chem. Abstracts," vol. 44, p. 8356e (1950).

*Primary Examiner*—Lewis Gotts
*Assistant Examiner*—S. P. Williams
*Attorney, Agent, or Firm*—Sughrue, Rothwell, Mion, Zinn & Macpeak

[57] ABSTRACT

Pharmaceutically active L-tryptophane compounds comprising the compound of the formula:

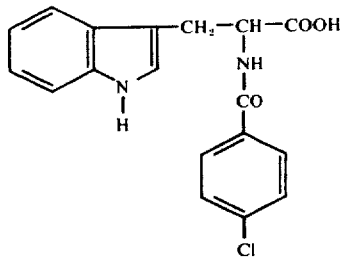

and its calcium, magnesium and aluminum salts.
These compounds exhibit superior pharmacologic activity on the gastroenteric tract.

8 Claims, No Drawings

N-P-CHLOROBENZOYL TRYPTOPHANE, SALTS AND COMPOSITIONS THEREOF

CROSS-REFERENCE TO RELATED APPLICATION

This application is a continuation-in-part of our earlier co-pending application Ser. No. 397,051, filed Sept. 13, 1973 and now abandoned and claims priority from May 18, 1971 based on Italian Patent Application Ser. No. 68652-A/71, said earlier co-pending application being in turn a continuation-in-part application of our still earlier application Ser. No. 222,668, filed Feb. 1, 1972, now abandoned.

The present invention relates to new derivatives of trypotophene, in the L, DL and D forms, which can be represented by formula

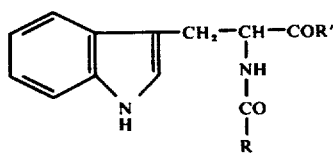

(I)

in which R may be:
1. — a phenyl group which is mono or polysubstituted at the ortho, meta or para positions with substituents chosen from the class comprising Cl, Br, F, I, CN, $NO_2$, $NH_2$ OH, $OCH_3$, COOH, $COOC_2H_5$, $CH_3$, $C_2H_5$, $CF_3$;
2. — a mono or polysubstituted benzyloxy group with substituents chosen from the class indicated under 1);
3. — a mono or polysubstituted benzyl group with substituents chosen from the class indicated under 1);
4. — a hydroxynaphthyl group; and in which R' may be
   A. — a hydroxyl group;
   B. — an aniline group having at the para position a carboxyl group or a carboxyl group esterified with an aliphatic $C_1$–$C_6$ linear or branched alcohol, with benzyl alcohol, or with a phenol such as ordinary phenol or 2,4-dichlorophenol;
   C. — an amine group substituted with a phenylacetic acid group as such or esterified with one of the alcohols listed under B);
   D. — an alkoxy group terminating with a secondary or tertiary amine group, free or salified with a mineral acid such as for example hydrochloric acid or with an organic acid such as for example citric or oxalic acid.

These compounds show interesting pharmacological properties with respect to mammals. One of such properties is a high antispastic effect on the smooth muscle system of the gastroenteric tract; another property is a regulating effect on gastric secretion, particularly an antisecretive effect in the cases of hypersecretion; yet another property is a protective and cicatrising effect on the gastroenteric mucosa. The aforesaid compounds can therefore be used to advantage in various diseases attacking the digestive system of man, originating in fact from disturbances in gastric secretion and spasms and lesions of the mucosa, such as for example gastroduodenal or peptic ulcers or colitis.

The invention particularly relates to the compound:

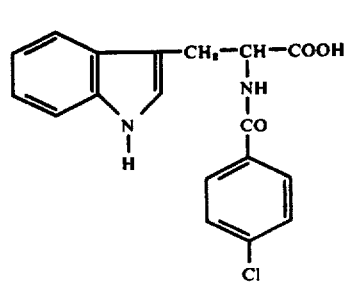

(I')

and its Ca, Mg and Al salts, as this compound and salts possess certain highly useful, unpredictable therapeutical properties which will be evidenced hereinafter. The compound (I'), which chemically is N-p-chlorobenzoyl-L-tryptophane, will also be briefly denoted herein "CR501".

The compounds of type 1-A may be prepared by condensation of the tryptophane with a chloride of an aromatic acid, which may be mono or polysubstituted in the phenyl ring, at a temperature between approximately −5° C and approximately +10° C, and preferably at around +5° C, in the presence of a hydroxide, carbonate or bicarbonate of an alkali metal or alkaline earth metal (which serves both to salify the carboxyl function of the tryptophane and as a hydrochloric acid acceptor) or in the presence of a tertiary organic base. The chloride of the acid may be added as such or dissolved in a solvent miscible with water (for example dioxane, tetrahydrofuran) or, preferably, immiscible with water (ethyl acetate). The reaction time may vary from approximately half-an-hour up to 24 hours; in general, the reaction may be said to have ended after 12 hours. At this point in the first two cases, the impurities are extracted with an organic solvent; in the third case, the aqueous phase is separated from the organic phase which contains the impurities.

The end product, which is dissolved as a salt of an alkali metal or alkaline earth metal in the aqueous phase, is precipitated by acidification, filtered and, possibly, crystallised.

The compounds of type 2-A may be prepared by condensation of tryptophane with a carbobenzoxychloride, which may be substituted, similarly to the compounds of type 1-A, or by reaction between tryptophane and an azidoformate of the mono or polysubstituted aryl alcohol.

The compounds of type 3-A and 4-A are prepared in a manner similar to that used for type 1-A.

The compounds in which R' belongs to class B) are obtained from the corresponding compounds having R' in class A) by condensation with the appropriate ester of the p-aminobenzoic acid (and possibly subsequent hydrolysis) in the presence of a solvent and of a condensing agent, at a temperature between 0° C and 25° C (preferably 12° to 15° C). The reaction time varies from 2 to 40 hours; on average 12 hours are sufficient. The solvent is typically ethyl acetate, chloroform, dimethylsulphoxide, dimethylformamide, dioxane or tetrahydrofuran. The condensing agent is usually a carboimide, for example dicyclohexylcarboimide, or carbonyldiimidazole. At the conclusion of reaction, the mixture is filtered, the filtrate is brought to dryness and taken up with ethyl acetate (if the reaction has not already been carried out in this solvent); the solution obtained is washed first with sodium bicarbonate solution, then with 2N hydrochloric acid or with citric acid, and finally with water, after which the moisture is eliminated and the result brought to dryness. The end product is obtained from the dry residue by recrystallisation.

Alternatively, the compounds in which R' belongs to Class B) may be obtained from the corresponding compounds having R' in Class A) by preparing a mixed anhydride of one of these latter compounds with an alkyl (ethyl, propyl, butyl, secondary butyl) chloroformate at a temperature between −20° C and 0° C, preferably at −10° C, in an anhydrous solvent of the same type as those used in condensation of the carbodiimides already mentioned here. Then, by reacting the mixed anhydride with an appropriate ester of p-aminobenzoic acid at a temperature between −5° C and +15° C (preferably at +5° C), the desired amide is obtained. In order to obtain the free acid, the ester group is hydrolysed with dilute NaOH in aqueous alcohol at a temperature between 15° C and 40° C (preferably 25° C) for a time varying from half an hour to 12 hours (preferably 4 hours).

The compounds of type 1-C, 2-C, 3-C and 4-C are obtained from the corresponding compounds of type 1-A, 2-A, 3-A, 4-A by condensation, under the same conditions as already described, with the appropriate ester of 4-aminophenylacetic acid and possible hydrolysis of the ester group.

In addition, the compounds of types 1-B, 1-C, 3-B, 3-C can be obtained also from compounds 2-B, 2-C, 4-B, 4-C by catalytic hydrogenation and subsequent benzoylation or phenylacetylation, respectively. In addition, the compounds of types 1-B, 1-C, 3-B, 3-C having a free carboxyl function can also be obtained from corresponding benzyl esters by catalytic hydrogenation in alcohol or aqueous alcohol, in the presence or absence of acetic acid, working at ambient temperature and in the presence of a hydrogenation catalyst (for example palladium oxide chloride); when hydrogenation is finished, the length of time required ranging from half-an-hour to approximately 6 hours, filtration is performed via the catalyst, the filtrate is brought to dryness and the product is crystallised from a solvent.

The compounds of group 1-D, 2-D, 3-D, 4-D are obtained by condensation among compounds 1-A, 2-A, 3-A, 4-A with the appropriate aminoalcohol in the presence of a carbodiimide, such as dicyclohexylcarbodiimide at a temperature between 0° C and 25° C, preferably 12° to 15° C, in a solvent such as ethyl acetate, chloroform, dimethyl sulphoxide, dimethylformamide, dioxane or tetrahydrofuran. Upon completion of reaction, the filtrate is brought to dryness and taken up again with acetone, and by the addition of an acetone or ether solution of the appropriate mineral or organic acid, the salt of the desired compound is precipitated.

The compounds of type 1-D, 2-D, 3-D, 4-D may be obtained by reaction between the sodium salts of the compounds 1-A, 2-A, 3-A, 4-A, and the appropriate chlorobases in toluene under reflux. The organic solution is concentrated to dryness after washing and elimination of moisture, the residue is taken up again with acetone or ethyl ether, and an acetone or ether solution of the appropriate mineral or organic acid is added.

In the examples below, Ar is a benzene ring and R is

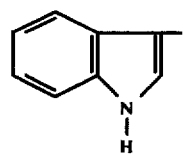

EXAMPLE 1

N-p-chloro-carbobenzoxy-L-tryptophane

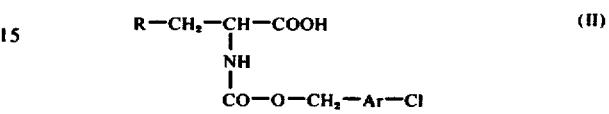

To a solution of 30 g (0.147 mols) L-tryptophane in 147 ml of 1N NaOH, maintained at 5° C, are added at the same time a further 147 ml of 1N NaOH and 30.06 g (0.147 mols) of p-chloro-carbobenzoxy chloride dissolved in 150 ml ethyl acetate. Agitation continues for 12 hours. The aqueous layer is separated from the organic layer and acidified; N-p-chloro-carbobenzoxy-L-tryptophane is precipitated and separated by filtration. Melting point 124° to 126° C. 48.2 g obtained. Yield 88%.

EXAMPLE 2

N-m-chloro-carbobenzoxy-L-tryptophane

The procedure is the same as in Example 1, m-chloro-carbobenzoxy chloride being used instead of p-chloro-carbobenzoxy chloride. Yield 84%. Melting point 107° to 108° C.

EXAMPLE 3

N-o-chloro-carbobenzoxy-L-tryptophane

The procedure is the same as in Example 1, o-chloro-carbobenzoxy chloride being used. Yield 81%. Melting point 97° to 99° C.

EXAMPLE 4

N-p-chloro-carbobenzoxy-DL-tryptophane

The same procedure is used as in Example 1, DL-tryptophane being used instead of L-tryptophane. Yield 85%. Melting point 178° to 180° C.

EXAMPLE 5

N-p-chloro-carbobenzoxy-D-tryptophane

The same procedure is used as in Example 1, D-tryptophane being used instead of L-tryptophane. Yield 83%. Melting point 132° to 133° C.

EXAMPLE 6

N-p-bromo-carbobenzoxy-L-tryptophane

The same procedure is used as in Example 1, p-bromo-carbobenzoxy chloride being used. Yield 79%. Melting point 141° to 142° C.

EXAMPLE 7

N-p-iodo-carbobenzoxy-L-tryptophane

The same procedure is used as in Example 1, using p-iodo-carbobenzoxy chloride. Yield 80%. Melting point 170° to 172° C.

EXAMPLE 8

N-p-cyano-carbobenzoxy-L-tryptophane

The same procedure is used as in Example 1, p-cyano-carbobenzoxy chloride being used. Yield 82%. Melting point 111° to 112° C.

EXAMPLE 9

N-p-methyl-carbobenzoxy-L-tryptophane

The same procedure is used as in Example 1, p-methyl-carbobenzoxy chloride being used. Yield 77%. Melting point 75° to 77° C.

EXAMPLE 10

N-p-ethyl-carbobenzoxy-L-tryptophane

The same procedure is used as in Example 1, p-ethyl-carbobenzoxy chloride being used. Yield 78%. Melting point 114° to 115° C.

EXAMPLE 11

N-p-trifluoromethyl-carbobenzoxy-L-tryptophane

The same procedure is used as in Example 1, p-trifluoromethyl-carbobenzoxy chloride being used. Yield 77%. Melting point 146° to 147° C.

EXAMPLE 12

N-p-nitro-carbobenzoxy-L-tryptophane

The same procedure is used as in Example 1, p-nitro-carbobenzoxy chloride being used. Yield 82%. Melting point 134° to 135° C.

EXAMPLE 13

N-(2,4-dichloro)-carbobenzoxy-L-tryptophane

The same procedure is used as in Example 1, 2,4-dichloro-carbobenzoxy chloride being used. Yield 74%. Melting point 138° to 139° C.

EXAMPLE 14

N-(2,6-dichloro)-carbobenzoxy-L-tryptophane

The same procedure is used as in Example 1, 2,6-dichloro-carbobenzoxy chloride being used. Yield 47%. Melting point 132° to 133° C.

EXAMPLE 15

N-(2,3-dichloro)-carbobenzoxy-L-tryptophane

The same procedure is used as in Example 1, 2,3-dichloro-carbobenzoxy chloride being used. Yield 53%. Melting point 146° to 147° C.

EXAMPLE 16

N-(3,4-dichloro)-carbobenzoxy-L-tryptophane

The same procedure is used as in Example 1, 3,4-dichloro-carbobenzoxy chloride being used. Yield 56%. Melting point 144° to 145° C.

EXAMPLE 17

N-(3-chloro-4-methyl)-carbobenzoxy-L-tryptophane

The same procedure is used as in Example 1, 3-chloro-4-methyl-carbobenzoxy chloride being used. Yield 57%. Melting point 132° to 133° C.

EXAMPLE 18

N-p-chloro-benzoyl-L-tryptophane

The same procedure is used as in Example 1, p-chloro-benzoyl chloride being used. Yield 87%. Melting point 148° to 150° C.

EXAMPLE 19

N-p-bromo-benzoyl-L-tryptophane

The same procedure is used as in Example 1, p-bromo-benzoyl chloride being used. Yield 84%. Melting point 162° to 163° C.

EXAMPLE 20

N-p-trifluoromethyl-benzoyl-L-tryptophane

The same procedure is used as in Example 1, p-trifluoromethylbenzoyl chloride being used. Yield 78%. Melting point 160° to 161° C.

EXAMPLE 21

N-p-toluyl-L-tryptophane

The same procedure is used as in Example 1, p-toluyl chloride being used. Yield 88%. Melting point 149° to 151° C.

EXAMPLE 22

N-p-toluyl-D-tryptophane

The same procedure is used as in Example 1, p-toluyl chloride and D-tryptophane being used. Yield 82%. Melting point 146.5° to 147.5° C.

EXAMPLE 23

N-p-toluyl-DL-tryptophane

The same procedure is used as in Example 1, p-toluyl chloride and DL-tryptophane being used. Yield 82%. Melting point 217.5° to 218.5° C.

EXAMPLE 24

N-p-cyano-benzoyl-L-tryptophane

The same procedure is used as in Example 1, p-cyano-benzoyl chloride being used. Yield 87%. Melting point 125° to 127° C.

EXAMPLE 25

N-p-fluoro-benzoyl-L-tryptophane

The same procedure is used as in Example 1, p-fluoro-benzoyl chloride being used. Yield 86%. Melting point 85° to 87° C.

EXAMPLE 26

N-p-methoxy-benzoyl-L-tryptophane

The same procedure is used as in Example 1, p-methoxy-benzoyl chloride being used. Yield 67%. Melting point 63° to 65° C.

EXAMPLE 27

N-p-carboxy-benzoyl-L-tryptophane

The same procedure is used as in Example 1, p-carboxy-benzoyl chloride being used. Yield 81%. Melting point 187° to 189° C.

EXAMPLE 28

N-p-amino-benzoyl-L-tryptophane

This is prepared from the corresponding nitroderivative (see Example 29 which follows) by catalytic reduction. Yield 63%. Melting point 207° to 209° C.

EXAMPLE 29

N-p-nitro-benzoyl-L-tryptophane. $C_2H_5OH$

This compound contains a molecule of ethanol of crystallisation. It is prepared according to Example 1, p-nitro-benzoyl chloride being used in place of p-chloro-carbobenzoxy chloride. Yield 92%. Melting point 115° to 117° C.

EXAMPLE 30

N-m-chloro-benzoyl-L-tryptophane

The same procedure is used as in Example 1, m-chloro-benzoyl chloride being used. Yield 73%. Melting point 160° to 161° C.

EXAMPLE 31

N-(carbo-alpha-naphthyl-methoxy)-L-tryptophane

The same procedure is used as in Example 1, carbo-alpha-naphthylmethoxy chloride being used. Yield 62%. Melting point 169° to 171° C.

EXAMPLE 32

N-p-methoxy-carbobenzoxy-L-tryptophane

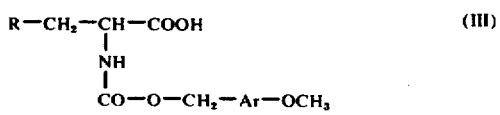

3.47 g of L-tryptophane (0.017 mols) are stirred together with 1.37 g (0.0183 mols) of magnesium oxide in 20 ml of water. The mixture is cooled to 7° C and a solution of 3.4 g (0.017 mols) of p-methoxy-carbobenzoxy azide $H_3CO-C_6H_4-CH_2OCON_3$ in 20 ml of dioxane are added dropwise. Agitation is continued for 24 hours. The result is diluted with 150 ml of water and brought to a pH of 6.9 with 1N HCl, and then to pH 3 with 10% citric acid. It is extracted with ethyl acetate, the extract is washed with water until a neutral reaction is achieved, the moisture is eliminated, and the result is concentrated to a small volume. The product is precipitated by the addition of petroleum ether. Product obtained 4.63 g. Yield 74%. Melting point 103° to 104° C.

EXAMPLE 33

Ethyl-N-carbobenzoxy-L-tryptophyl-p-aminobenzoate

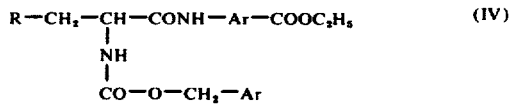

3 g (0.0086 mols) N-carbobenzoxy-L-tryptophane are dissolved in 30 ml of dioxane and 1.465 g (0.00886 mols) of ethyl p-aminobenzoate and 1.855 g (0.00887 mols) dicyclohexylcarbodiimide are added. Agitation is continued for 12 hours at 14° C. The result is filtered via the precipitate and the filtrate is brought to dryness. The dry residue is taken up again with ethyl acetate. The organic solution is extracted with 2N hydrochloric acid, then with sodium bicarbonate, and washed with water, and the moisture is eliminated and the result concentrated to a small volume. The product is precipitated by the addition of petroleum ether. Product obtained 3.8 g. Yield 86%. Melting point 154° to 155° C.

EXAMPLE 34

2,4-Dichlorophenyl-N-carbobenzoxy-L-tryptophyl-p-aminobenzoate

The same procedure is used as in Example 33, 2,4-dichlorophenyl p-aminobenzoate being used instead of ethyl p-aminobenzoate. Yield 78%. Melting point 199° to 201° C.

EXAMPLE 35

Phenyl-N-carbobenzoxy-L-tryptophyl-p-aminobenzoate

The same procedure is used as in Example 33, phenyl p-aminobenzoate being used. Yield 80%. Melting point 190° to 192° C.

EXAMPLE 36

Benzyl-N-carbobenzoxy-L-tryptophyl-p-aminobenzoate

The same procedure is used as in Example 33, benzyl-p-aminobenzoate being used. Yield 91%. Melting point 160° to 162° C.

EXAMPLE 37

Ethyl-N-benzoyl-L-tryptophyl-p-aminobenzoate

The same procedure is used as in Example 33, N-benzoyl-L-tryptophane being used. Yield 82%. Melting point 181° to 183° C.

EXAMPLE 38

Methyl-N-carbobenzoxy-L-tryptophyl-p-aminophenylacetate

The same procedure is used as in Example 33, methyl-p-aminophenyl-acetate being used. Yield 76%. Melting point 98° to 99° C.

EXAMPLE 39

Benzyl-N-carbobenzoxy-L-tryptophyl-p-aminophenylacetate

The same procedure is used as in Example 33, benzyl p-aminophenyl acetate being used. Yield 82%. Melting point 128° to 130° C.

EXAMPLE 40

Methyl-N-benzoyl-L-tryptophyl-p-aminophenylacetate

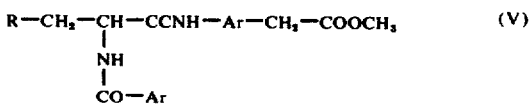

6.17 g (0.02 mols) of N-benzoyl-L-tryptophane are dissolved in 80 ml anhydrous tetrahydrofuran; the result is cooled to −10° C and 2.02 g (0.02 mols) of triethylamino are added. Still at −10° C, 2.17 g (0.02 mols) of ethyl chlorocarbonate are added. The temperature is maintained at −10° C for 30 minutes and then 3.3 g (0.02 mols) of methyl 4-aminophenylacetate are added, dissolved in 100 ml tetrahydrofuran. The mixture is left at 5° C for five hours, brought to dryness and the residue taken up again with ethyl acetate. It is washed with 2N HCl, then with sodium bicarbonate, finally with water, and the moisture removed. By concentration to a small volume and the addition of petroleum ether, the product is precipitated. Product obtained 7.75 g. Yield 85%. Melting point 173° to 174° C.

EXAMPLE 41

N-benzoyl-L-tryptophyl-p-aminophenylacetic acid

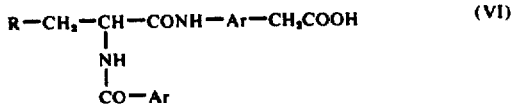

7 g (0.0154 mols) of methyl-N-benzoyl-L-tryptophyl-phenylacetate are dissolved in 400 ml absolute ethanol and 30 ml of water and 23.1 ml 1N NaCH are added. The reaction mixture is left at 25° C for 4 hours and then concentrated at 35° C in a vacuum; the residue is taken up again with ethyl acetate and extracted with water. By acidification with 2N hydrochloric acid, the product is precipitated and, after separation and drying, crystallised with benzene. Product obtained 5.5 g. Yield 81%. Melting point 169° to 171° C.

EXAMPLE 42

N-benzoyl-L-tryptophyl-p-aminobenzoic acid

The same procedure is used as in Example 41, methyl-N-benzoyl-L-tryptophyl-benzoate being used instead of the phenylacetate mentioned. Yield 73%. Melting point 271° to 273° C.

EXAMPLE 43

N-Carbobenzoxy-L-tryptophyl-p-aminobenzoic acid

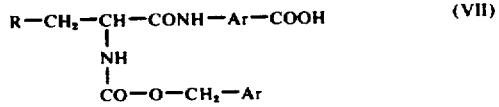

5.475 g (0.01 mols) benzyl-N-carbobenzoxy-L-tryptophyl-p-aminobenzoate (see Example 36) are dissolved in 180 ml of methyl alcohol to which 3 drops of glacial acetic acid and 600 mg 5% palladium oxide have been added. A stream of hydrogen is bubbled through the mixture for 4 hours, the result is filtered and the filtrate concentrated to a small volume. The addition of ethyl ether precipitates L-tryptophyl-p-aminobenzoic acid (melting point 252° to 253° C). Product obtained 2.85 g, representing a yield of 91%.

2.4 g (0.00744 mols) of this acid are dissolved in 7.44 ml 1N NaOH and at the same time a further 7.44 ml 1N NaOH and 1.27 g (0.00744 mols) of benzyl chloroformate dissolved in 17 ml ethyl acetate are added dropwise, the temperature being maintained at 5° C. The reaction is allowed to continue for 12 hours; the aqueous phase is separated and from this, by precipitation with 2N HCl, the desired product is obtained (3.06 g). Yield 90%. Melting point 186° to 189° C.

EXAMPLE 44

N-carbobenzoxy-L-tryptophyl-p-aminophenylacetic acid

The same procedure is used as in Example 43, benzyl-N-carbobenzoxy-L-tryptophyl-p-aminophenylacetate being used (see Example 39). Yield 86%. Melting point 134° to 136° C.

EXAMPLE 45

N-p-bromobenzoyl-L-tryptophyl-phenylacetic acid

The same procedure is used as in Example 41, methyl-N-p-bromobenzoyl-L-tryptophyl-phenylacetate being used. Yield 77%. Melting point 136° to 138° C.

EXAMPLE 46

N-p-chlorobenzoyl-L-tryptophyl-phenylacetic acid

The same procedure is used as in Example 41, methyl-N-p-chlorobenzoyl-L-tryptophyl-phenylacetate being used. Yield 74%. Melting point 125° to 127° C.

EXAMPLE 47

N-p-chlorophenylacetyl-L-tryptophane

The same procedure is used as in Example 1, using p-chloro-phenylacetyl chloride. Yield 91%. Melting point 214° to 214.5° C.

EXAMPLE 48

Dimethylaminoester of N-p-chlorocarbobenzoxy-L-trytophane hydrochloride

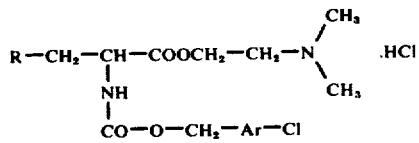

3.728 g (0.01 mols) of N-p-chlorocarbobenzoxy-L-trytophane (see Example 1) are added to 30 ml of toluene and 230 mg (0.01 mols) metallic sodium. The mixture is heated for 2 hours at 50° C, cooled to 25° C and 1.085 g (0.01 mols) dimethylaminoethanechloride Cl-CH$_2$-N(CH$_2$-N(CH$_3$)$_2$ dissolved in 15 ml toluene are added. The result is heated for 12 hours at 80° C and cooled; the organic layer is separated and washed with water, and after elimination of the moisture, is brought to dryness; and the residue is taken up again with ether. Addition of ether saturated with gaseous MCl precipitates the hydrochloride which is crystallised from ethyl alcohol. Product obtained 4.3 g. Yield 89%. Melting point 110° to 112° C.

EXAMPLE 49

Diethylaminoethylester of N-p-toluyl-L-tryptophane oxalate 3.728 g (0.01 mols) of N-p-toluyl-L-tryptophane (see Example 21) have added to them 50 ml ethyl acetate containing 2.0632 g (0.01 mols) of dicyclohexylcarbodiimide and 1.17 g (0.01 mols) 2-diethylaminoethanol. The mixture is left for 12 hours at 12° C, filtered via dicyclohexylurea and the filtrate extracted with sodium bicarbonate. After elimination of the moisture, the liquid is brought to dryness, the residue is taken up again with acetone, and the oxalate is precipitated by the addition of oxalic acid in acetone. The product is crystallised from isopropyl alcohol. Yield 82%. Melting point 117° to 119° C.

EXAMPLE 50

N-o-chlorobenzoyl-L-tryptophane

The same procedure is used as in Example 1, o-chlorobenzoyl chloride being used. Yield 88%. Melting point 65° to 76° C.

EXAMPLE 51

N-o-chlorobenzoyl-DL-tryptophane

The same procedure is used as in Example 1, o-chlorobenzoyl chloride and DL-tryptophane being used. Yield 84%. Melting point 56° to 70° C.

EXAMPLE 52

N-o-chlorobenzoyl-D-tryptophane

The same procedure is used as in Example 1, o-chlorobenzoyl chloride and D-tryptophane being used. Yield 83%. Melting point 74° to 83° C.

Table 1 which follows summarizes the main properties of the compounds described in the foregoing Examples, particularly the antisecretive activity, which is bereft of any anticolinergic component; this activity is particularly interesting in that it is manifest at relatively low doses.

| Compound | $DL_{50}$ value *1 | Activity A *2 | Activity B *3 |
|---|---|---|---|
| Ex. 1 (CR449) | 240 | 131 | 127 |
| Ex. 2 (CR527) | 450 | 176 | 147 |
| Ex. 3 (CR460) | 640 | 118 | 267 |
| Ex. 4 (CR463) | 217 | 161 | 130 |
| Ex. 5 (CR630) | 260 | 142 | 107 |
| Ex. 6 (CR451) | 125 | 92.1 | 77 |
| Ex. 7 (CR490) | 166 | 75 | 94 |
| Ex. 8 (CR496) | 1070 | 201.8 | 340.5 |
| Ex. 9 (CR454) | 320 | 186.7 | 125 |
| Ex.10 (CR500) | 158 | 142 | 117 |
| Ex.11 (CR515) | 175 | 112 | 92 |
| Ex.12 (CR438) | 700 | 267.2 | 195 |
| Ex.13 (CR470) | 170 | 130 | 97 |
| Ex.14 (CR495) | 268 | 132 | 108 |
| Ex.15 (CR499) | 175 | 100 | 60 |
| Ex.16 (CR469) | 208 | 137 | 104 |
| Ex.17 (CR497) | 190 | 231 | 196 |
| Ex.18 (CR501) | 263 | 139 | 110 |
| Ex.19 (CR503) | 360 | 111 | 85 |
| Ex.20 (CR505) | 210 | 160 | 110 |
| Ex.21 (CR510) | 700 | 184 | 318 |
| Ex.22 (CR556) | 365 | 354 | 190 |
| Ex.23 (CR555) | 340 | 204 | 172 |
| Ex.24 (CR512) | 1450 | 500 | 360 |
| Ex.25 (CR506) | 655 | 223 | 295 |
| Ex.26 (CR507) | 1000 | 437 | 494 |
| Ex.27 (CR508) | 900 | 514 | 406 |
| Ex.28 (CR504) | 1670 | 960 | 205 |
| Ex.29 (CR502) | 806 | 339 | 270 |
| Ex.30 (CR546) | 560 | 210 | 147 |
| Ex.31 (CR514) | 160 | 128 | 94 |
| Ex.32 (CR462) | 430 | 146 | 114 |
| Ex.33 (CR401) | 1000 | 470 | 320 |
| Ex.34 (CR432) | 1000 | 370 | 310 |
| Ex.35 (CR411) | 1000 | 610 | 460 |
| Ex.36 (CR430) | 1000 | 690 | 520 |
| Ex.37 (CR402) | 1000 | 310 | 460 |
| Ex.38 (CR417) | 1000 | 300 | 300 |
| Ex.39 (CR419) | 1000 | 430 | 350 |
| Ex.40 (CR418) | 1000 | 290 | 180 |
| Ex.41 (CR421) | 1000 | 322 | 186 |
| Ex.42 (CR404) | 500 | 284 | 220 |
| Ex.43 (CR422) | 460 | 321 | 180 |
| Ex.44 (CR435) | 980 | 370 | 210 |
| Ex.45 (CR511) | 690 | 246 | 281 |
| Ex.46 (CR589) | 295 | 189 | 120 |
| Ex.47 (CR584) | 545 | 487 | 270 |
| Ex.48 (CR583) | 210 | 170 | 121 |
| Ex.49 (CR636) | 320 | 160 | 120 |
| Ex.50 (CR617) | 1270 | 299 | 255 |
| Ex.51 (CR618) | 1400 | 345 | 320 |
| Ex.52 (CR637) | 1530 | 440 | 390 |

*1 $DL_{50}$ in the mouse mg/kg iv.
*2 Anti-secretive activity in the rat with lig. pylorus $ED_{50}$ mg/kg iv.
*3 Anti-secretive activity in the rat by gastric stimulus, $ED_{50}$ mg/kg oral.

Another characteristic feature of the present compounds is a considerable difference in toxicity between intravenous administration and administration by mouth, while the therapeutic activity remains unaltered; thus, the therapeutic coefficient is greatly increased, and hence the tolerability of the compounds themselves when administered to man by mouth (Table 2).

TABLE 2

Examples of differences between toxicity ($DL_{50}$ in the mouse) by intravenous administration and oral administration in mg/kg. Variation in therapeutic coefficient

| 1 Compound | 2 $DL_{50}$ iv | 3 Activity *3 | 4 Coefficient *4 | 5 $DL_{50}$ oral | 6 Activity *6 | 7 Coefficient *7 |
|---|---|---|---|---|---|---|
| Ex.18 (501) | 263 | 139 | 1.9 | 1100 | 150 | 7.3 |
| Ex. 1 (449) | 240 | 131 | 1.8 | 1410 | 154 | 9.1 |
| Ex. 6 (451) | 185 | 99 | 1.9 | — | 133 | — |
| Ex. 9 (454) | 320 | 166 | 1.9 | — | 268 | — |
| Ex.21 (510) | 700 | 184 | 3.8 | 2000 | 346 | 5.8 |
| Ex.32 (462) | 430 | 133 | 3.2 | | 142 | — |

*3 Anti-secretive activity $ED_{50}$ i.v. mg/kg
*4 Therapeutic coefficient iv. 2/3
*6 Anti-secretive activity $ED_{50}$ oral
*7 Therapeutic coefficient oral Particularly marked is the anti-spastic activity which the present compounds exercise on the entire digestive system. Measured in the mouse, using the vegetable carbon test (rate of transit through the stomach and intestine), this activity is in some cases comparatively greater than the anti-secretive activity (Table 3).

TABLE 3

Example of anti spastic activity of the compounds compared with the anti-secretive activity. Values in mg/kg of body weight

| 1 Compound | 2 Anti-spastic activity $ED_{50}$ mg/kg | 3 Anti-secretive activity $ED_{50}$ mg/kg | 3/2 Ratio 3/2 |
|---|---|---|---|
| Ex.18 (501) | 82 | 139 | 1.7 |
| Ex. 1 (449) | 72 | 131 | 1.8 |
| Ex. 3 (468) | 58 | 118 | 2.0 |
| Ex. 9 (454) | 120 | 187 | 1.6 |
| Ex.30 (617) | 300 | 299 | 1 |
| Ex.41 (421) | 170 | 322 | 2.0 |

The tolerance to prolonged administration has been confirmed by suitable experiments on animals in the case of some of these compounds. It is therefore possible to use them in the treatment of humans in various pathological situations, for example in spastic and painful syndromes in general, particularly conditions of the digestive system, gastric and duodenal ulcers, gastritis and duodenitis.

Pharmaceutical forms of the compounds according to the invention may be prepared by conventional techniques. For many of these (for example CR501 - Ex. 18), tablets containing 100 mg each of the compound may be prepared and used to advantage, as well as phials for intramuscular administration, each containing 150 mg of the compound.

On average, the oral forms may contain from 50 to 300 mg of compound, while those for parenteral administration may contain from 100 to 250 mg.

Salts of CR.501 (N-p-chloro-benzoyl-L-tryptophane)
and of CR.449
(N-p-chloro-carbobenzoxy-L-tryptophane)

EXAMPLE 53

N-p-chloro-benzoyl-L-tryptophane calcium salt.

A solution of 34.2 g (0.1 moles) of N-p-chlorobenzoyl-L-tryptophane in 1,000 ml of 0.1 N NaOH, kept at room temperature, was quickly admixed while stirring with 6.05 g (0.11 equiv.) of $CaCl_2$ previously dissolved in 100 ml $H_2O$. The N-p-chlorobenzoyl-L-triptophane starts precipitating forthwith in the form of calcium salt. The reaction mass is stirred during two hours at least to allow the precipitate of conveniently enlarging in volume. The resulting precipitate is filtered and washed with water till chlorine ions disappear. The product is dried in a circulating air oven at 90° C during 12 hours. 34.4 g product are obtained.

Yield 93% melting point 280°–285° C with slow decomposition. The product contains two molecules crystallization water. Crystallizes from a mixture of 2 vol. parts acetone with 3 vol. parts water. Very slightly soluble in $H_2O$, soluble in methanol, ethanol, acetone.

EXAMPLE 54

N-p-chloro-carbobenzoxy-L-tryptophane calcium salt.

The procedure is similar to Example 53; 37.2 g (0.1 equiv.) of N-p-chlorocarbobenzoxy-L-tryptophane are employed instead of the N-p-chloro-benzoyl-L-tryptophane. 34.5 g product are obtained.

Yield 90%. Melting point 217°–221° C with slow decomposition. The product crystallizes from acetone - water mixture (1:1 by volume).

Very slightly soluble in water, soluble in methanol and ethanol.

EXAMPLE 55

N-p-chloro-benzoyl-L-tryptophane magnesium salt.

The procedure is similar to Example 53, by using 10.5 g (0.105 equiv.) of $MgCl_2 \cdot 6 H_2O$ instead of calcium chloride. 32.5 g salt are obtained.

Yield 92%. Melting point 210°–215° C. The product crystallizes from acetone — water mixture (1:1 by volume). Very slightly soluble in water, soluble in methanol and ethanol.

EXAMPLE 56

N-p-chloro-benzoyl-L-tryptophane aluminium salt.

The procedure is similar to example 53. Instead of calcium chloride 8.45 g (0.105 equiv.) of $AlCl_3 \cdot 6 H_2O$ are used. 31.5 g salt are obtained. Yield 88%. Melting point 188°–195° C with slow decomposition. The product crystallizes from acetone - $H_2O$ mixture (1:1).

Soluble in methanol and ethanol, very slightly soluble in $H_2O$.

EXAMPLE 57

N-p-chloro-benzoyl-L-tryptophane sodium salt.

A solution of 34.2 g (0.1 moles) N-p-chloro-benzoyl-L-tryptophane dissolved in a mixture of 240 ml acetone and 10 ml $H_2O$ is admixed while stirring with 0.105 equivalents $Na_2CO_3 \cdot 10 H_2O$. The reaction mixture is stirred at 60° C during 2 hours (necessary period of time for full solubilization of the reactants), whereupon it is cooled to room temperature and poured while stirring into 500 ml ethyl ether. The resulting precipitate is filtered and dried in an air oven at 70° C during 12 hours. 35 g salt are obtained.

Yield 96%. Melting point 228°–231° C. Water solubility about 5%. Highly soluble in methanol, ethanol and acetone.

EXAMPLE 58

N-p-chloro-carbobenzoxy-L-tryptophane sodium salt.

The procedure is similar to Example 57; 37.2 g (0.1 moles) N-p-chloro-carbobenzoxy-L-tryptophane are used instead of N-p-chlorobenzoyl-L-tryptophane. 37.4 g salt are obtained.

Yield 95%. Melting point 224°–227° C water solubility about 5%. Highly soluble in methanol, ethanol and acetone.

EXAMPLE 59

N-p-chloro-benzoyl-L-tryptophane calcium salt.

40.8 g (0.2 moles) L-tryptophane are suspended in 100 ml deionized $H_2O$ admixed with 8 g (0.2 moles) NaOH tablets dissolved in 200 ml deionized $H_2O$. The temperature of the resulting solution is lowered to 13°–14° C and during 1 to 3 hours, preferably about 2 hours) 26 ml (0.2 moles) of p-chloro-benzoyl chloride dissolved in 80 ml tetrahydrofurane and 200 ml 1N NaOH are dripped thereinto. The reaction temperature is kept during dripping between 14° C and 18° C. Stirring is carried out during 12 hours and the temperature is not allowed to sink below 14° C in order to avoid the formation of a precipitate.

The resulting solution is shaken twice during a period of 15 minutes with 250 ml ethyl acetate and 250 ml isopropylether, respectively, the organic phase being discarded every time. A solution of 12.0 g $CaCl_2$ (0.11 equiv.) in 200 ml deionized water is quickly dripped at room temperature into the remaining aqueous solution.

On completion of dripping the reaction mass is stirred at room temperature during two hours at least to allow of the formed precipitate to conveniently enlarge in volume. The filtered precipitate is taken-up twice with 600 and 400 ml deionized water, respectively, filtered and dried in an air oven at 90° C during 12 hours. 68.2 g salt are obtained.

Yield 90%. Refer to Example 53 in respect of chemical - physical properties.

Table 1

| PHARMACOLOGICAL TESTS Comparison of antisecretive activity | | | | |
|---|---|---|---|---|
| | Antisecretive activity | | | |
| Compound | 2.5 hrs | 5 hrs | 10 hrs | 15 hrs |
| CR 501 | 171 | 143 | 150 | 361 |
| CR 501 calcium salt | 210 | 165 | 142 | 170 |
| CR 501 aluminium salt | 195 | 152 | 150 | 163 |
| CR 501 magnesium salt | 230 | 180 | 146 | 135 |
| CR 501 sodium salt | 118 | 141 | 147 | 410 |
| CR 449 | 121 | 98 | 115 | 155 |
| CR 449 calcium salt | 142 | 112 | 110 | 106 |
| CR 504 (Ex. 28) | 1075 | 1090 | 1490 | >2000 |
| CR 504 - Calcium salt | 1480 | 1865 | >2000 | >2000 |
| CR 438 (Ex. 12) | 475 | 560 | 980 | >1500 |
| CR 438 - Calcium salt | 810 | 780 | 972 | >1500 |
| CR 451 (Ex. 6) | 180 | 148 | 133 | 405 |
| CR 451 - Calcium salt | 233 | 220 | 337 | 580 |
| CR 510 (Ex. 21) | 490 | 407 | 346 | 583 |

Table 1-continued

PHARMACOLOGICAL TESTS
Comparison of antisecretive activity

| Compound | Antisecretive activity | | | |
|---|---|---|---|---|
| | 2.5 hrs | 5 hrs | 10 hrs | 15 hrs |
| CR 510 - Calcium salt | 602 | 574 | 521 | 666 |

(*)The antisecretive activity is defined as the dose in mg/kg of body weight of the animal, which reduces the gastric secretion by 50%. The evaluation is effected by considering the decrease in quantity of secreted gastric juice as compared with controls. Rats of an average weight of 200 ± 20 grams are employed of which the lower part of the stomach at the level of the pylorus is tied to collect the gastric juice during the indicated periods. The preparations are administered orally in the form of an aqueous suspension.

COMMENTS

The antisecretive activity of CR 501 starts before 5 hours from administration and extends up to 15 hours with a gradual sinking.

The activity of the calcium, aluminum and magnesium salts is somewhat delayed but much more durable as compared to, for example, activity of the sodium salt, probably due to the water solubility of the sodium salt.

Table 2
Comparison of the protective activity of CR 501, and salts thereof

| Compound | $ED_{50}$ mg/kg/os |
|---|---|
| CR 501 | 234 |
| CR 501 calcium salt | 145 |
| CR 501 aluminium salt | 174 |
| CR 501 magnesium salt | 162 |
| CR 501 sodium salt | 210 |
| CR 449 | 182 |
| CR 449 calcium salt | 121 |
| Calcium carbonate (140mg/kg) | |
| Aluminium hydroxide (136mg/kg) | inactive |
| CR 504 (Ex. 28) | >1500 |
| CR 504 - Calcium salt | >1500 |
| CR 438 (Ex. 12) | 990 |
| CR 438 - Calcium salt | >1500 |
| CR 451 (Ex. 6) | 335 |
| CR 451 - Calcium salt | 392 |
| CR 510 (Ex. 21) | 382 |
| CR 510 - Calcium salt | 390 |

The activity is defined as the dose in mg/kg of body weight to the animal, which prevents in 50% of the treated subjects arising of lesions due to Indomenthacin.

Indomenthacin is orally administered to rats of an average weight of 200 ± 20 grams by a dose of 16 mg/kg. After 4 hours all the controls exhibit haemoragic gastric lesions.

The protective preparations are administered orally in aqueous suspension.

COMMENTS

It is noted that CR 501 exhibits an efficient activity in preventing gastric lesions from Indomethacin. However, the salts exhibit an improved activity, probably due to their longer residence in the cells of the mucose.

This activity is not exerted by the cation, because the latter is present in each salt in a very small quantity by weight. In fact, administration of other salts of calcium or aluminum containing the cation in a quantity even ten times as much as that of the salts of CR 501 does not exhibit any therapeutical activity in this experimental ulcera.

Table 3
Comparison of antispastic activity of CR 501 and salts thereof

| Compound | $ED_{50}$ mg/kg |
|---|---|
| CR 501 | 248 |
| CR 501 calcium salt | 210 |
| CR 501 aluminium salt | 270 |
| CR 501 magnesium salt | 278 |
| CR 501 sodium salt | 192 |
| CR 501 sodium salt i.p. | 82 |
| CR 504 (Ex. 28) | >1000 |
| CR 504 - Calcium salt | >1000 |
| CR 438 (Ex. 12) | 870 |
| CR 438 - Calcium salt | >1000 |
| CR 451 (Ex. 6) | 275 |
| CR 451 - Calcium salt | 393 |
| CR 510 (Ex. 21) | 487 |
| CR 510 - Calcium salt | 725 |

(*)The antispastic activity is measured in mice of an average weight of 22 ± 3 g by administering a suspension of charcoal in gum arabic and checking after two hours whether the charcoal has reached the initial portion of the colon. In non-treated subjects the charcoal reaches this very point. When a drug is active as antispastics it slows down the transit of the charcoal. Evaluation of the results is effected as $ED_{50}$ in mg/kg body weight of the animal, i.e., the dose at which the charcoal has not reached the colon in 50% of the treated animals.

COMMENTS

CR 501 is active as antispastic even when it is orally administered as a water-insoluble powder. So are the likewise water-insoluble salts of calcium, aluminum and magnesium.

SUMMARY OF ACTIVITIES

It will also be seen in Tables 1, 2 and 3 that our claimed, water-insoluble salts (particularly Ca-salt) of CR501 exhibit therapeutical properties sharply superior to their unsalified parent compound (CR501). This is a surprisingly anamalous behavior when compared with similar salts of other compounds disclosed hereinbefore. To evidence this anomaly Tables 1, 2 and 3 include, as comparative examples, values ascertained for compounds such as CR438, CR451, CR504 and CR510 and their calcium salts (not claimed herein). As will be seen from Table 1, the antisecretive activity is substantially more durable when employing calcium, aluminium and magnesium salts which therefore exhibit as compared with the acid CR 501, the advantage of an improved therapeutical activity.

As will be seen from Table 2 these calcium, aluminum and magnesium salts further exhibit a higher protective activity which does not depend upon their cation content (as cation dosages even ten times larger than the one administered with the CR 501 salt result ineffective per se).

It will be seen from Table 3 that the calcium salt as compared with the other salts and the parent compound is more particularly effective as antispastic and is therefore recommendable for use as antiulcera in the cases of duodenal ulcera complicated by spasms.

THERAPEUTICAL USE

Therapeutical forms: oral forms

Both with CR 501 and its salts oral pharmaceutical forms are recommended. Oral forms are all those which may be technically obtained more particularly gelatine capsules and simple tablets obtained by pressing the powder admixed with pharmaceutically acceptable excipients.

The advisable dosage in each tablet or capsule ranges from 150 to 300 mg.

With these forms the calcium salt is more particularly recommended as it exhibits on conventional preservation tests thorough stability and absence of light sensitiveness which is partly present in certain other salts or in the compound not brought to salt form.

DOSAGE

The minimum recommendable dose is 450 mg daily by three distinct administrations spaced in time, each of mg 150. However, when necessary the dosage may be doubled or trebled.

PARENTHERAL FORMS

Vials comprising a solution in water and with a pharmaceutically acceptable water-miscible solvent It is thereby possible to solubilize CR501 which is otherwise insoluble in water. By way of example but not of limitation of the choice of the water-miscible solvent the following formula is suggested.

| CR 501 | mg 150 |
|---|---|
| propylene glycol | ml 1.2 |
| bidistilled water q.s. | ml 2 |

Manner of administration: owing to the presence of a solvent these vials can be used only for intramuscular injection.

DOSAGE: the administration of one or more (three at the utmost) vials daily is advisable.

SUPPOSITORY PHARMACEUTICAL FORMS

Both CR 501 and salts thereof can be rectally administered in the form of suppositories.

The dosage is possible in suppositories containing 150 mg or 300 mg of CR 501 or salts thereof combined with pharmaceutically acceptable excipients.

DOSAGE: one to three suppositories daily spaced during the day or the night.

TOLERABILITY

CR 501 and salts thereof, more particularly its calcium salt by oral administration were investigated as to acute and chronical toxicity on two species of animals (rat and dog) without exhibiting any appreciable symptom of toxicity even with dosages (mg/kg) twenty times those recommended for human therapy.

Similarly, theratogenesis tests on New Zealand rabbits did not show any fatal toxicity.

In humans the prolonged oral administration of CR 501 calcium salt over several weeks with doses ranging from 500 to 1600 mg does not lead to any specific side effect.

Similarly, the administration of vials by intramuscular route does not cause any particular disturbances.

Although the present invention has been adequately described in the foregoing specification and Examples included therein, it is obvious that additional changes and modifications may be made thereto without departing from the spirit and scope thereof.

What we claim is:

1. A pharmaceutically active L-tryptophane compound of the formula:

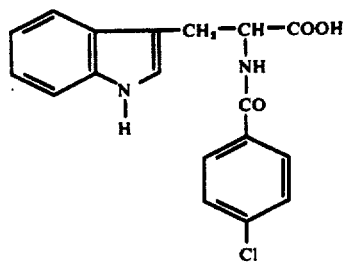

and its Ca, Mg and Al salts.

2. The calcium salt of N-p-chlorobenzoyl-L-tryptophane.

3. A pharmaceutical composition for treating gastroenteric disturbances comprising, as active substance, an L-tryptophane compound of the formula:

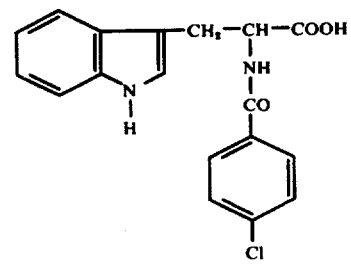

or its Ca, Mg or Al salt, in combination with a pharmaceutically acceptable inert carrier.

4. The pharmaceutical composition of claim 3 in unit dosage form comprising from 50 to 300 mg of said compound or salt.

5. The composition of claim 4 in orally administerable form, containing 150–300 mg of said compound or salt.

6. The composition of claim 4 in the form of a suppository containing 150–300 mg of said compound or salt.

7. A pharmaceutical composition in orally administerable unit dosage form for treating gastro-enteric disturbances, comprising the calcium salt of N-p-chlorobenzoyl-L-tryptophane in an amount of 150–300 mg, in combination with a pharmaceutically acceptable inert carrier.

8. The calcium, magnesium or aluminum salt of a pharmaceutically active L-tryptophane compound of the formula:

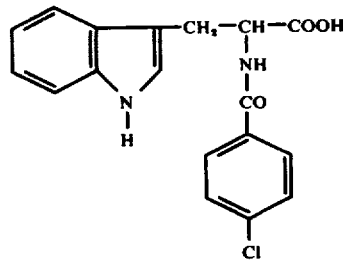

* * * * *